US007254425B2

(12) United States Patent
Lowery et al.

(10) Patent No.: US 7,254,425 B2
(45) Date of Patent: Aug. 7, 2007

(54) METHOD FOR DETECTING ARTIFACTS IN DATA

(75) Inventors: Michael G. Lowery, Wildwood, IL (US); Eric B. Shain, Glencoe, IL (US); Omar S. Khalil, Libertyville, IL (US)

(73) Assignee: Abbott Laboratories, Abbott Park, IL (US)

( * ) Notice: Subject to any disclaimer, the term of this patent is extended or adjusted under 35 U.S.C. 154(b) by 308 days.

(21) Appl. No.: 10/763,548

(22) Filed: Jan. 23, 2004

(65) Prior Publication Data
US 2005/0165316 A1 Jul. 28, 2005

(51) Int. Cl.
*A61B 5/00* (2006.01)
(52) U.S. Cl. ............... 600/310; 600/336; 600/316; 600/480
(58) Field of Classification Search .......... 600/336, 600/310, 322, 330, 316
See application file for complete search history.

(56) References Cited

U.S. PATENT DOCUMENTS

| | | | | |
|---|---|---|---|---|
| 4,955,379 | A | * | 9/1990 | Hall ........................ 600/336 |
| 5,485,838 | A | * | 1/1996 | Ukawa et al. ............. 600/330 |
| 5,766,127 | A | * | 6/1998 | Pologe et al. ............. 600/310 |
| 5,782,757 | A | | 7/1998 | Diab et al. |
| 6,002,952 | A | * | 12/1999 | Diab et al. ................. 600/310 |
| 6,002,957 | A | | 12/1999 | Finneran |
| 6,018,673 | A | | 1/2000 | Chin et al. |
| 6,067,462 | A | | 5/2000 | Diab et al. |
| 6,236,872 | B1 | | 5/2001 | Diab et al. |
| 6,241,663 | B1 | | 6/2001 | Wu et al. |
| 6,353,226 | B1 | | 3/2002 | Khalil et al. |
| 6,374,129 | B1 | | 4/2002 | Chin et al. |
| 6,501,975 | B2 | * | 12/2002 | Diab et al. ................ 600/336 |

(Continued)

FOREIGN PATENT DOCUMENTS

WO  95/21565  8/1995

(Continued)

OTHER PUBLICATIONS

Hayes et al., "Artifact reduction in photoplethysmography", Applied Optics, vol. 37, No. 31, Nov. 1, 1998; pp. 7437-7446.

(Continued)

*Primary Examiner*—Eric F. Winakur
(74) *Attorney, Agent, or Firm*—Merchant & Gould P.C.

(57) ABSTRACT

A method for identifying artifacts occurring during a measurement of the concentration of an analyte in a biological sample by means of an apparatus that employs temperature-controlled optical probes, introduces electromagnetic radiation into tissue, and collects and detects radiation emitted at a distance from the point at which the electromagnetic radiation is introduced. The values of intensity of radiation emitted at different wavelengths, at different distances between the light introduction site(s) and the light collection site(s), and at different temperatures are collected and used in the method to generate a relationship between these values and the concentration of an analyte in the tissue or the disease state of a patient. The method involves the use of an algorithm that identifies artifacts in the data resulting from motion of the patient and allows the rejection of data sets that contain these artifacts. The algorithm identifies sudden changes in the magnitude and direction in a sequence of collected signals.

12 Claims, 15 Drawing Sheets

U.S. PATENT DOCUMENTS

| | | |
|---|---|---|
| 6,526,298 B1 | 2/2003 | Khalil et al. |
| 6,615,061 B1 | 9/2003 | Khalil et al. |
| 6,630,673 B2 | 10/2003 | Khalil et al. |
| 6,662,030 B2 | 12/2003 | Khalil et al. |
| 6,662,031 B1 | 12/2003 | Khalil et al. |
| 2003/0023151 A1 | 1/2003 | Khalil et al. |

FOREIGN PATENT DOCUMENTS

| | | |
|---|---|---|
| WO | 99/59464 | 11/1999 |
| WO | 02/060320 | 8/2002 |
| WO | 02/082989 | 10/2002 |

OTHER PUBLICATIONS

Gostt et al., "Real-Time Pulse Oximetry Artifact Annotation on Computerized Anaesthetic Records", Journal of Clinical Monitoring and Computing, vol. 17; pp. 249-257, 2002.

Rhee, "Design and Optimization of an Artifact-Resistive Wearable Photoplethysmographic Device: The Ring Sensor", Doctoral Thesis Proposal, Department of Mechanical Engineering of the Massachusetts Institute of Technology, Aug. 1999.

The PCT Search Report for PCT/US04/041029, Jul. 2005.

The PCT Search Report.

Yeh et al., "Monitoring Blood Glucose Changes in Cutaneous Tissue by Temperature-modulated Localized Reflectance Measurements". Clinical Chemistry, vol. 49:6, 2003; pp. 924-934.

Yeh et al., "Near-infrared thermo-optical response of the localized reflectance of intact diabetic and nondiabetic human skin". Journal of Biomedical Optics, vol. 8, No. 3, Jul. 2003; pp. 534-544.

Khalil et al., "Temperature modulation of the visible and near infrared absorption and scattering coefficients of human skin". Journal of Biomedical Optics, vol. 8, No. 2, Apr. 2003; pp. 191-205.

Wu et al., "Noninvasive Determination of Hemoglobin and Hematocrit Using a Temperature-Controlled Localized Reflectance Tissue Photometer". Analytical Biochemistry, vol. 287, 2000; pp. 284-293.

Zhang et al., "Investigation of Noninvasive in vivo Blood Hematocrit Measurement Using NIR Reflectance Spectroscopy and Partial Least-Squares Regression". Applied Spectroscopy, vol. 54, No. 2, 2000; pp. 294-299.

Khalil et al., Method for Modulating Light Penetration Depth in Tissue and Diagnostic Applications Using Same, U.S. Appl. No. 09/419,461, filed Oct. 15, 1999.

\* cited by examiner

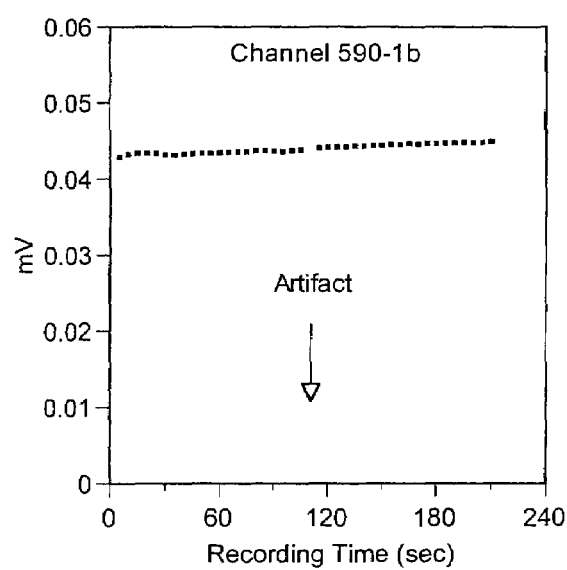
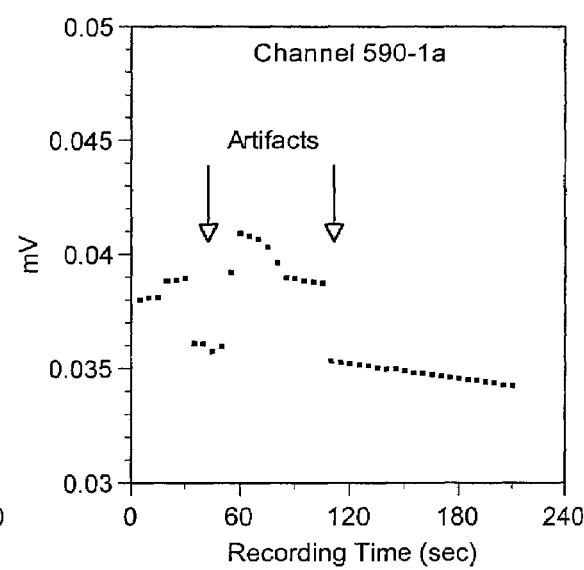
FIG. 2C
FIG. 2D

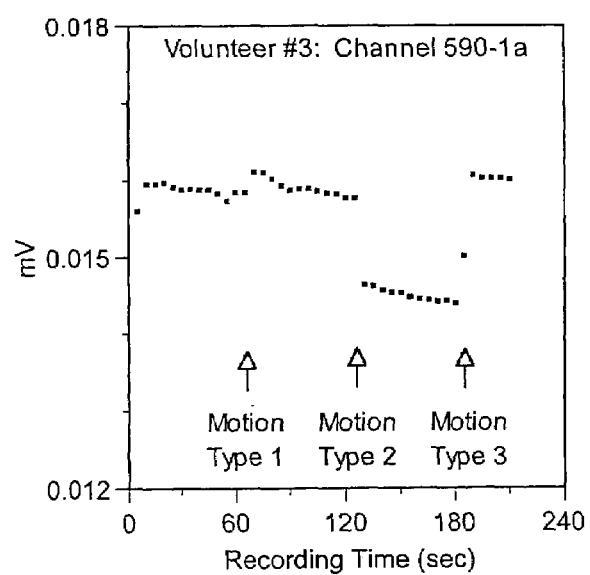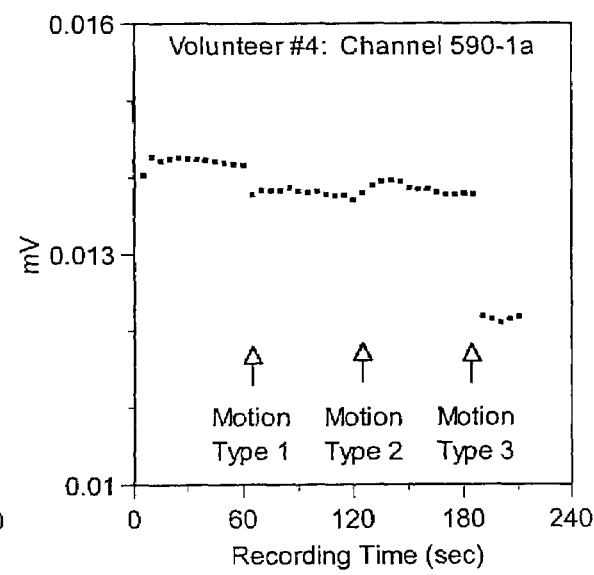
FIG. 3C
FIG. 3D

METHOD FOR DETECTING ARTIFACTS IN DATA

BACKGROUND OF THE INVENTION

1. Field of the Invention

This invention relates to a method for detecting artifacts in data, more particularly, data observed during physiological testing.

2. Discussion of the Art

U.S. Pat. No. 6,526,298 discloses an apparatus and method for measuring the concentration of an analyte (such as glucose) within a biological tissue. The method involves the steps of controlling the temperature of the tissue, introducing electromagnetic radiation into the tissue, and measuring the intensity of the electromagnetic radiation emitted from the surface of the tissue. The period of contact between the apparatus and the tissue lasts several minutes. Optical data from a plurality of channels of the apparatus are recorded at regular time intervals during each measurement. See FIGS. 1A, 1B, 1C, and 1D, which show various trends of data. The optical data, which are converted to voltage levels by a photodetector, are used to determine the concentration of an analyte, based on empirical models.

A successful determination of the concentration of an analyte requires proper thermal and optical contact between an optical probe and the surface of the tissue. Example of such devices are described U.S. Pat. No. 6,241,663; U.S. Pat. No. 6,353,226; U.S. Pat. No. 6,526,298; U.S. Pat. No. 6,615,061; U.S. Pat. No. 6,662,030; U.S. Pat. No. 6,662,031; WO 99/59464; WO 2002/060320A1; WO 2002/082989A1; U.S. Ser. Nos. 09/419,461, filed Oct. 15, 1999, and 09/834,440, filed Apr. 13, 2001; and Khalil, et al., "Temperature modulation of the visible and near infrared absorption and scattering coefficients of intact human skin", *J. Biomedical Optics*, 8(2), 191-205 (April 2003); Yeh, et al., "Near-infrared thermo-optical response of the localized reflectance of intact diabetic and non-diabetic human skin", *J. Biomedical Optics*, 8(3), 534-544 (July 2003); and Yeh, et al., "Monitoring Blood Glucose Changes in Cutaneous Tissue by Temperature-modulated Localized Reflectance Measurements", *Clinical Chemistry* 49:6 924-934 (2003).

The preferred optical probe is a combination optical/thermal head that contacts the tissue. The probe preferably comprises a thermally conductive temperature-controlled disc, preferably made of aluminum, and a fiber-optic bundle at the center of the disc. Failure to maintain proper contact between the probe and the surface of the tissue can result in artificial perturbations (artifacts) in some or all of the recorded data. See FIGS. 2A, 2B, 2C, and 2D, which show various artifacts occurring in trends of data. An artifact can result in an erroneous calculation of the concentration of the analyte because the artifact distorts the actual trend of the intensity of the radiation emitted over a period of time. Contact between the apparatus and the tissue can be compromised by improper application of the probe to the surface of the tissue, by accidental movement of the probe or the tissue during the measurement, and perhaps by any substances on the surface of the tissue that interfere with the collection of radiation emitted.

Clinical tests employing a prototypical dual-sensor probe on the volar forearm of 20 diabetics produced at least 37 results (out of 400 tests) having data artifacts that were deemed unacceptable for glucose modeling. Most of these artifacts were assumed to result from human error by the patient or by the clinician and cannot be totally prevented. Some patients experienced a percentage of artifacts much higher than average.

It is believed that a primary cause of data artifacts is movement of the forearm during a measurement. In a confirmatory measurement, subjects were instructed to remain motionless during each measurement, except at one-minute intervals, when they intentionally moved their forearms (in contact with the probe) in a specified manner. The movements generally coincided with the production of artifacts in the optical signals, as shown in FIGS. 3A, 3B, 3C, and 3D.

Mathematical detection of artifacts with the apparatus is difficult, because the optical data can exhibit numerous trends that are unpredictable. FIGS. 1A, 1B, 1C, and 1D depict normal data that move in an upward trend, in a downward trend, in a horizontal trend, sometimes changing direction or modulating during a test, respectively. Causes of these variations include the difference in the temperature of the probe and the initial temperature of the tissue, changes in optical properties of the tissue as the temperature of the tissue changes, variations in properties of the tissue among the population (optical, thermal, structural, etc.), and variations in the biological responses to temperature of the probe among the population. FIGS. 2A, 2B, 2C, and 2D depict how the data artifacts can differ in magnitude and direction.

Methods for identifying motion artifacts are known in the art of photoplethysmography, namely where measurements in which a periodic signal associated with the heartbeat is monitored over a long period of time, typically in recovery, intensive care, and emergency rooms. The algorithm for detection of motion artifacts depends on differentiating the periodicity of the true signal and non-periodicity of the motion-induced erratic signal. Techniques such as Fourier transform are used to assign a frequency to the periodic signals and reject the non-periodic signals. Examples of this approach are shown in U.S. Pat. Nos. 6,018,673 and 6,374,129. Another approach is the signal extraction technology described in U.S. Pat. Nos. 5,782,757; 6,002,952; 6,067,462; and 6,236,872. However, a problem arises when the detection method does not depend on the heartbeat and the sequence of data points has no inherent periodicity. This problem is particularly apparent in the case of the non-invasive determination of the concentration of glucose, or continuous monitoring of hematocrit, involving the use of methods described in U.S. Pat. No. 6,662,031; Zhang et al., "Investigation of Noninvasive in Vivo Blood Hematocrit Measurement Using NIR Reflectance Spectroscopy and Partial Least Squares Regression", Applied Spectroscopy, Vol. 54, No. 2, 2000, pp. 294-299; and Wu et al., "Noninvasive Determination of Hemoglobin and Hematocrit Using a Temperature-Controlled Localized Reflectance Tissue Photometer", Anal. Biochem., 287, 284-293 (2000).

It would be desirable to develop a method for detecting artifacts in order to alert the user that a measurement may be erroneous and that a repeat measurement is necessary. Such a method would be useful for preventing data points corresponding to artifacts from being included in subsequent calculations for the non-invasive determination of the concentrations of analytes, such as, for example, hemoglobin, hematocrit, and glucose.

SUMMARY OF THE INVENTION

This invention provides a method for identifying artifacts occurring during a measurement of the concentration of an analyte in a biological sample by means of an apparatus that employs temperature-controlled optical probes, introduces electromagnetic radiation into tissue, and collects and detects radiation emitted at a distance from the point at which the electromagnetic radiation is introduced. The values of intensity of radiation emitted at different wavelengths, at different distances between the light introduction site(s) and the light collection site(s), and at different temperatures are collected and used in the method to generate a relationship between these values and the concentration of an analyte in the tissue or the disease state of a patient.

The method involves the use of an algorithm that identifies artifacts in the data resulting from motion of the patient and allows the rejection of data sets that contain these artifacts. The algorithm identifies sudden changes in the magnitude and direction in a sequence of collected signals. The algorithm incorporates features that mathematically compensate for the slope observed in a plot of data during an attempt to calculate the average value of the data.

In one aspect, the method comprises the steps of (a) providing an apparatus for measuring at least one optical property of the tissue;

(b) introducing electromagnetic radiation at at least one wavelength into the tissue by means of the apparatus;

(c) collecting optical data from the tissue over a selected period of time;

(d) introducing the collected data into an algorithm to identify an artifact in the data, the artifact resulting from movement of the probe or the tissue during a brief period of time; and (e) determining whether an artifact has appeared in the data.

In another aspect, the apparatus can provide a signal to an operator to indicate the occurrence of the artifact or to identify data that are suspected of containing an artifact.

In still another aspect, the algorithm employs a user-selected threshold and a slope parameter to detect motion artifacts in optical signals that do not depend on the periodicity of heartbeats.

The invention provides a safeguard against inclusion of erroneous data resulting from an inadvertent movement of a body part with respect to a measuring probe in a non-invasive optical measurement. Inclusion of erroneous data in the subsequent calculation of the concentration of a metabolite or of the determination of a disease state will lead to erroneous results and erroneous intervention that may adversely affect the health of a patient. Thus, the primary benefit of this invention is the generation of accurate and reliable data for the purpose of clinical diagnosis.

BRIEF DESCRIPTION OF THE DRAWINGS

FIGS. 2A, 2B, 2C, and 2D are graphs illustrating data recorded by a non-invasive analyte monitoring apparatus. The data in each of these graphs comprise an artifact.

FIGS. 3A, 3B, 3C, and 3D are graphs illustrating data recorded by a non-invasive analyte monitoring apparatus. The data in each of these graphs comprise at least one artifact. Each artifact was caused by intentional movement of the forearm.

DETAILED DESCRIPTION

Figures 1A, 1B:
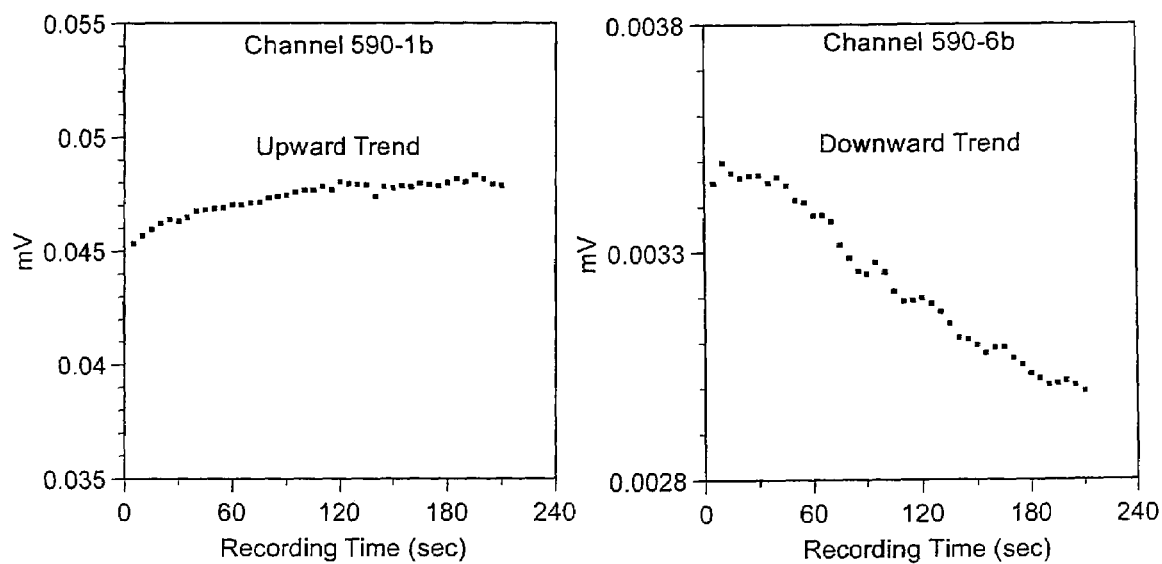
FIGS. 1A, 1B, 1C, and 1D are graphs illustrating data recorded by a non-invasive analyte monitoring apparatus. The data in these graphs are free of artifacts.
Figures 1C, 1D:
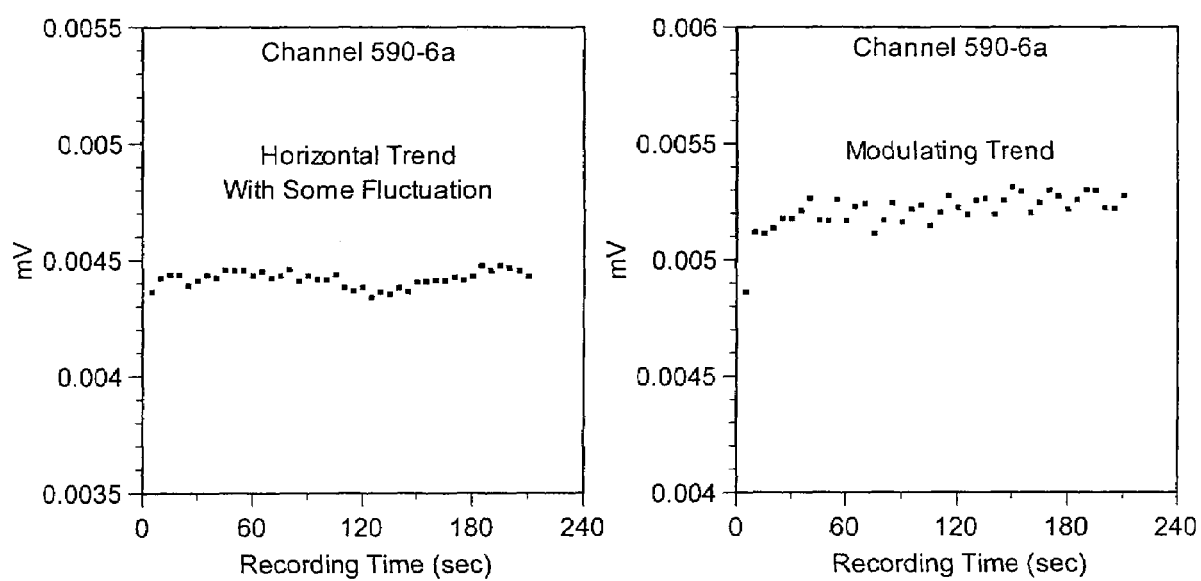
Figure 2A:
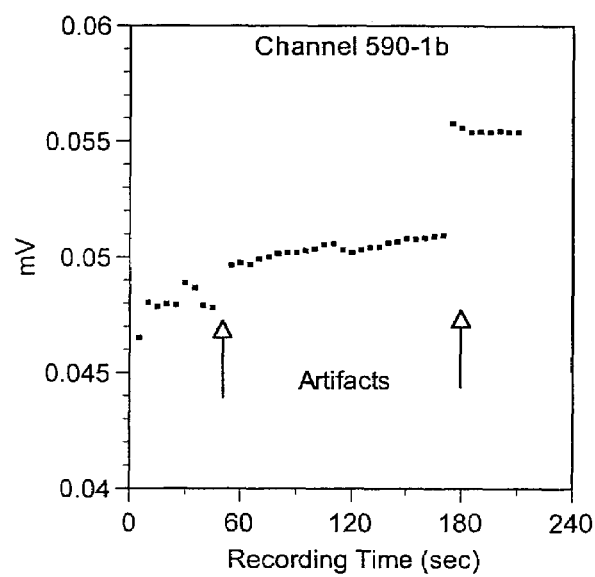
Figure 2B:
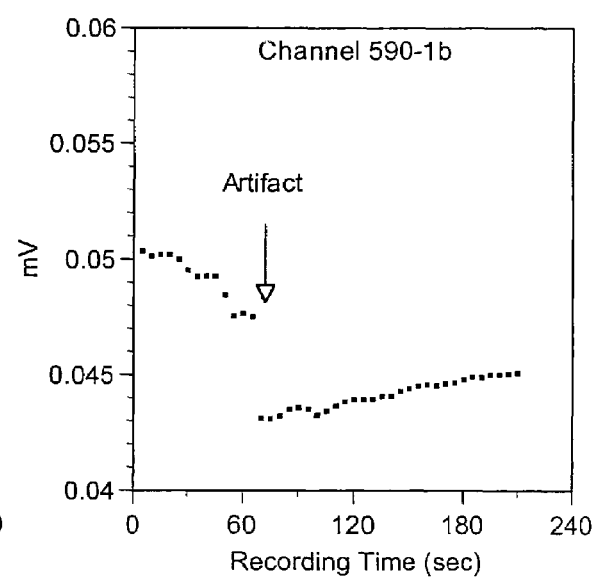
Figure 3A:
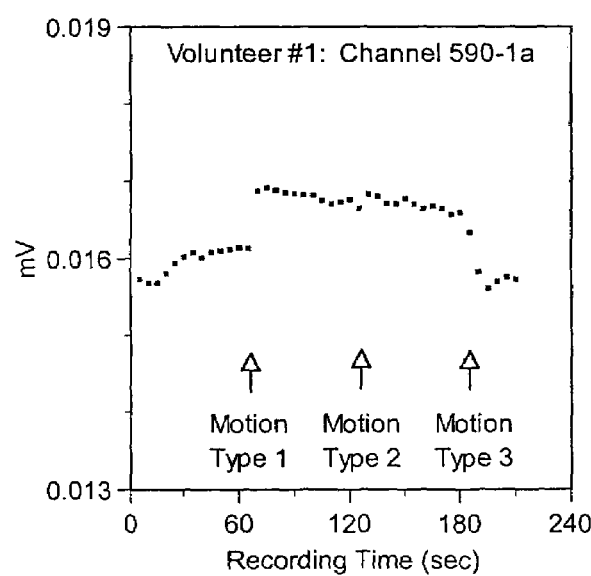
Figure 3B:
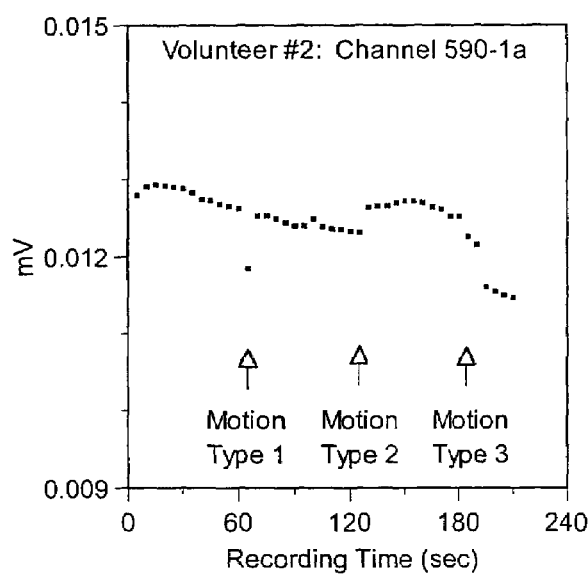

As used herein, the term "trend" means the general direction of the magnitude of the signal as a function of time; if the signal increases, the trend is upward; if the signal decreases the trend is downward. The term "probe" means an element that comprises at least one sensor for detecting and preferably measuring optical signals. The probe contacts the tissue during a measurement. In a preferred embodiment, the probe comprises a combined optical/thermal head in the form of an aluminum temperature-controlled disc having a fiber-optic bundle at the center of the disc. The term "sensor" means a device that detects a signal. The term "artifact" refers to a feature in the data that can result in an erroneous calculation of the concentration of the analyte. The artifact distorts the actual trend of the intensity of the radiation emitted over a period of time. The expression "motion artifact" refers to an artifact occurring within a brief period of time resulting from accidental movement of the optical probe or the tissue. A motion artifact typically causes a large perturbation in the optical data. The expression "intact human tissue" means a non-excised portion of tissue that is a part of an organ of a living patient. The expression "true data" means data that excludes motion artifacts. True data represents the actual signal that should be measured from intact human tissue. The expression "brief period of time" means the period of time required for making a measurement, which typically ranges up to three minutes.

This invention provides a method for identifying artifacts in optical measurements conducted for the purpose of determination of the concentration of analytes in tissue, the method comprising the steps of:

(a) providing an apparatus for measuring at least one optical property of the tissue;

(b) introducing electromagnetic radiation at at least one wavelength into the tissue by means of the apparatus;

(c) collecting optical data from the tissue over a selected period of time;

(d) introducing the collected data into an algorithm to identify an artifact in the data, the artifact resulting from movement of the probe or the tissue during a brief period of time; and (e) determining whether an artifact has appeared in the data.

The data obtained by this method can be used for the non-invasive determination of the concentrations of analytes in the human body; representative examples of these analytes are hemoglobin, hematocrit, and glucose. In a preferred embodiment, the apparatus can provide a signal to an operator to indicate the occurrence of the artifact or to identify data that are suspected of containing an artifact.

The method of this invention can be used with optical probes that are placed in contact with the tissue to collect a sequence of data points that are used for the purpose of determination of the concentration of an analyte, vital signs, and optical properties in intact human tissue. The method of this invention is preferably used with an apparatus for measuring reflectance, wherein at least one light introduction site is in contact with the skin of a subject and at least one light collection site is in contact with the skin of the subject. The processes of introduction of light and collection of light are preferably performed through the use of optical fibers, typically having major dimensions ranging from about 10 micrometers to about 500 micrometers. The method of this invention is particularly well-suited for this type of measurement, because an inadvertent motion can often result in loss of contact between an optical fiber of the probe at either a light introduction site or a light collection site. A loss of contact between the surface of the skin and a portion of the optical probe can result in an erroneous signal on account of the motion artifact. Inclusion of the erroneous signal in a subsequent calculation can lead to erroneous results.

Probes that are suitable for this purpose are described in detail in U.S. Pat. Nos. 6,526,298 and 6,630,673, incorporated herein by reference. The method of this invention can also be used with the method for the determination of vital signs and changes in the concentration of metabolite, described in U.S. Ser. No. 10/144,224, filed May 10, 2002, incorporated herein by reference. The method of this invention can be used with an apparatus for monitoring blood pressure, wherein a sequence of optical data for indicating a change in blood pressure is collected. The method of this invention can be used with an apparatus for monitoring blood oxygen saturation, wherein a sequence of optical data indicating a change in blood oxygen saturation is collected.

In the preferred embodiments of this invention, the electromagnetic radiation employed is in the range of from about 400 to about 2200 nm, preferably from about 400 to about 1100 nm.

The method of this invention employs an algorithm that identifies artifacts within the brief period of time in which they occur. Accidental movement of the probe or the tissue typically causes a significant perturbation in the optical data within several seconds of the time the data is recorded. A longer time period of approximately one (1) to three (3) minutes is required for intact human tissue, e.g., skin, to reach thermal equilibrium with the probe by heat conduction, as predicted by a detailed thermal model. Because the intensity of electromagnetic radiation emitted and collected varies with the temperature of the tissue, any significant change in intensity occurring within a period of one minute is a potential artifact. Minor exceptions include optical fluctuations on account of viscoelastic compression of tissue by the probe, vasodilatation, and other circulatory responses of the probe to temperature, but these fluctuations generally occur more gradually than do artifacts or they produce rapid perturbations that are insignificant in magnitude as compared with the artifacts.

Figure 4:
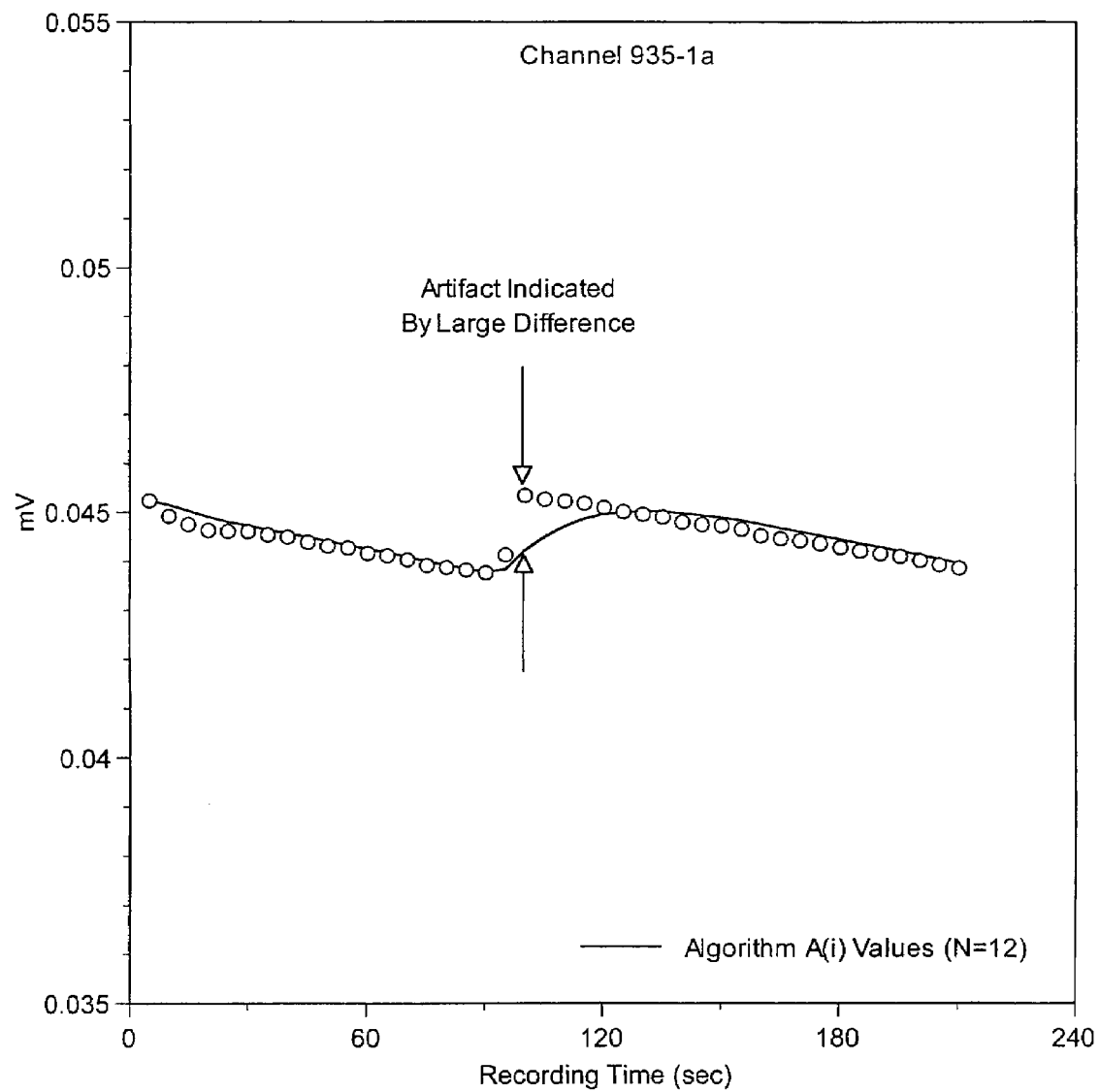
FIG. 4 is a graph illustrating identification of an artifact in data by the method of this invention.

The algorithm incorporates a time scale via a set of equations that process optical data from the apparatus. The equations, which are described below, are used to calculate a novel moving average value, $A(i)$, for test data from each individual channel of the apparatus. The data in a given time scale consists of the current data point (for which the value of $A(i)$ is being calculated) plus a fixed quantity of previously collected data points (N) selected for the calculations. For example, the algorithm can be applied over a time scale of 60 seconds to data that are recorded every 5 seconds; hence, $N=60/5=12$ data points. By selecting N in this manner, the values of $A(i)$ will closely follow the values of a series of data points recorded during a normal thermal/optical interaction between the tissue and the probe. Only when an artifact occurs will the value(s) of $A(i)$ begin to differ significantly from the values of the series of data points. FIG. 4 shows the indication of an artifact. An artifact is deemed detected when the absolute difference between the value of a data point and the corresponding value of $A(i)$ exceeds a threshold value (Dc), which is specified by the operator. The operator selects an appropriate threshold value for each channel, such that all significant artifacts are detected, while other minor fluctuations (resulting from vasodilatation, random noise, etc.) are excluded. Optimum selection of the appropriate threshold value can be determined by performing comprehensive calibration experimentation with the probe on a population of patients. The number of patients (e.g., 20 patients) should be selected to produce a good statistical sample within the population in terms of the observed range of vasodilation, random noise, etc. Such a number preferably ranges from about 20 to about 100, based on experience with populations of patients that show statistically significant results. Furthermore, the number of measurement per patient (e.g., 10 to 100) should be chosen to produce a good statistical sample of the observed test-to-test variation of vasodilation, random noise, etc. Such a number preferably ranges from about 10 to about 100, based on based on experience with populations of patients that show statistically significant results.

A novel feature of the algorithm is the slope parameter $S(i)$. This parameter enables the values of $A(i)$ to closely follow a series of data points having a non-zero slope. The slope parameter is important because the apparatus typically produces optical data that exhibit a trend upward or downward during a measurement. Failure of $A(i)$ to closely follow this data allows the detection of an artifact when the difference exceeds Dc.

The algorithm incorporates a time scale via a set of equations that process optical data from the apparatus. The equations, which are described below, are used to calculate a novel moving average value, $A(i)$, for test data from each individual channel of the apparatus. The data in a given time scale consists of the current data point (for which the value of $A(i)$ is being calculated) plus a fixed quantity of previously collected data points (N) selected for the calculations. For example, the algorithm can be applied over a time scale of 60 seconds to data that are recorded every 5 seconds; hence, $N=60/5=12$ data points. By selecting N in this manner, the values of $A(i)$ will closely follow the values of a series of data points recorded during a normal thermal/optical interaction between the tissue and the probe. Only when an artifact occurs will the value(s) of $A(i)$ begin to differ significantly from the values of the series of data points. FIG. 4 shows the indication of an artifact. An artifact is deemed detected when the absolute difference between the value of a data point and the corresponding value of $A(i)$ exceeds a threshold value (DC), which is specified by the operator. The operator selects an appropriate threshold value for each channel, such that all significant artifacts are detected, while other minor fluctuations (resulting from vasodilatation, random noise, etc.) are excluded. Optimum selection of the appropriate threshold value can be determined by performing comprehensive calibration experimentation with the probe on a population of patients. The number of patients (e.g., 20 patients) should be selected to produce a good statistical sample within the population in terms of the observed range of vasodilation, random noise, etc. Such a number preferably ranges from about 20 to about 100, based on experience with populations of patients that show statistically significant results. Furthermore, the number of measurement per patient (e.g., 10 to 100) should be chosen to produce a good statistical sample of the observed test-to-test variation of vasodilation, random noise, etc. Such a number preferably ranges from about 10 to about 100, based on experience with populations of patients that show statistically significant results.

Data from the equations (1), (2), (3) can be plotted on a point-by-point basis (i.e., in real time) for each series of optical data $X(i)$, beginning with the first point $X(1)$. $X(1)$ can be the first point recorded during a test, or a later point at which the calculations are to begin. The value of $A(i)$ calculated in equation (2) is similar to a conventional, exponential moving average of the data, with N being the quantity of points in the moving average. The key feature of the algorithm is the slope parameter $S(i)$. $S(i)$ represents an exponential moving average of the point-to-point change in the data $X(i)$, where N is the quantity of points in the moving average. $S(i)$ compensates for positive or negative slopes in the data, thereby enabling the values of $A(i)$ to closely follow the data rather than lag significantly. In other words, the use of $S(i)$ enables $A(i)$ to track the true data, i.e., data that is free of artifacts.

Given a series of N data points, each data point differs from the preceding data point by a calculated difference (positive or negative). This difference is called the point-to-point change in the data. The average value of the point-to-point change(s) observed among N data points is represented by $S(i)$. The equation for $S(i)$ specifies this average value according to a standard formula that is known as an exponential average. Therefore, $S(i)$ represents the average value of the slopes between adjacent data points. The algorithm uses $S(i)$ in the equations to adjust the values of $A(i)$ upwardly or downwardly in accordance with the average value of the slopes between adjacent data points. By moving upwardly and downwardly with the data, the values of $A(i)$ can more closely match values of true data that move in a trend upwardly or downwardly over a period of time. Failure of the values of $A(i)$ to move upwardly or downwardly with the data would result in the values of $A(i)$ differing too much from the true data, thereby resulting in an apparent "lag" between the values of $A(i)$ and the true data.

Data artifacts arising from the apparatus are distinguishable from artifacts arising from other sources by the rapid rate at which artifacts occur. Moving averages are sensitive only to the rate at which data changes from point to point regardless of the direction of the change.

Prior to developing the method of this invention, two conventional methods were used with optical data $X(i)$ obtained from individual channels. Both of these methods yielded similar results. These methods were the simple moving average and the exponential moving average. These methods are described below.

1. Simple Moving Average (SMA):

$$A(i)=\{\Sigma[X(j)]\}/N,$$

where $X(j)$ is summed from $(i-N+1)$ to $i$ and $i \geq N$.

2. Exponential Moving Average (EMA):

$$A(i)=[1-P]\cdot A(i-1)+P\cdot X(i),$$

where $P=2/[N+1]$ and $A(1)=X(1)$.

Figure 5:
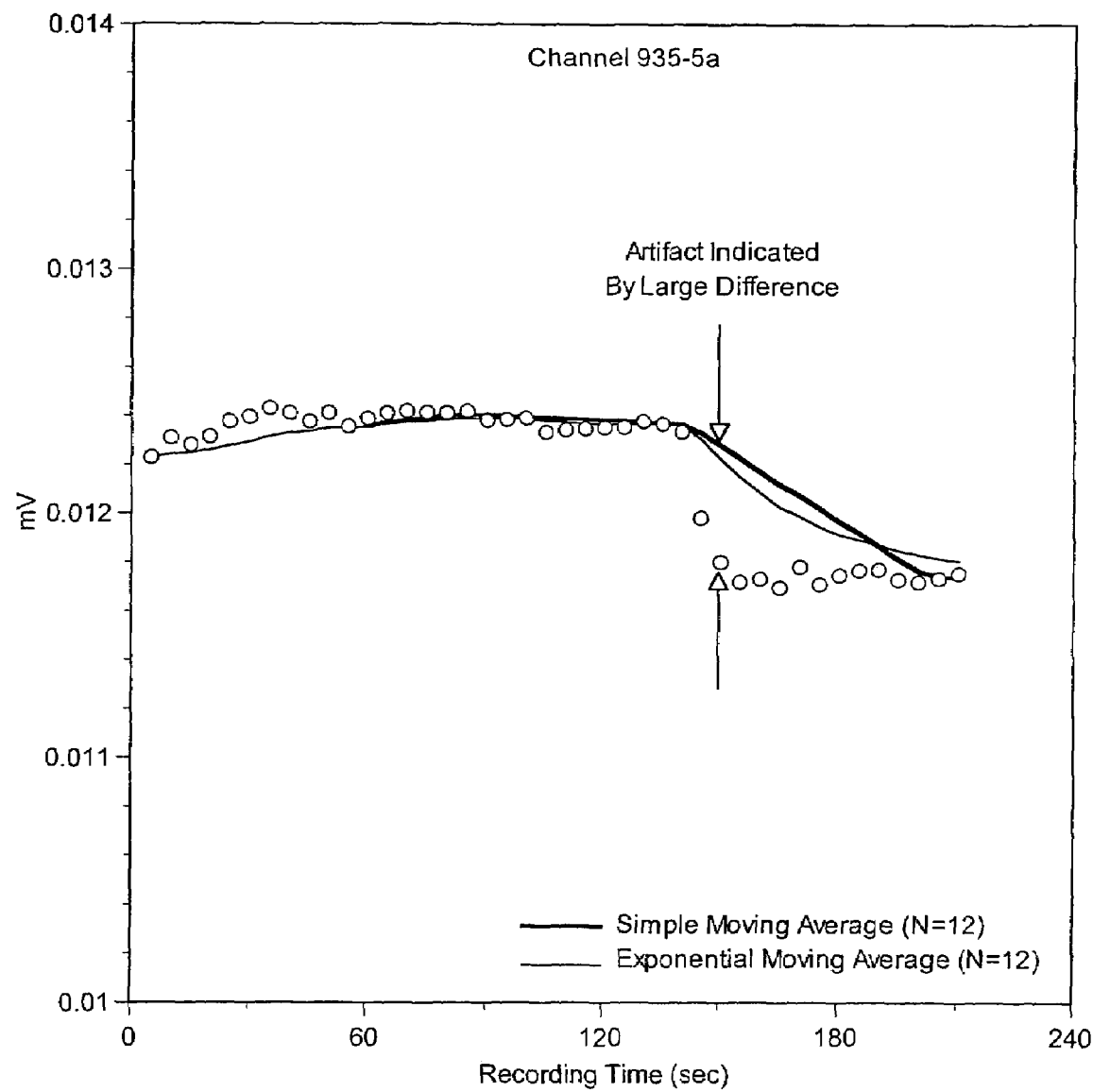
FIG. 5 is a graph illustrating identification of an artifact in data by a conventional moving average technique.

FIG. 5 depicts how SMA values and EMA values help to identify an artifact in a channel of data that exhibits a horizontal trend. The moving quantity of points (N) was set to 12 to incorporate a 60-second time scale as previously described. The values of SMA and EMA closely tracked the true data, except during the occurrence of the artifact, where a large difference resulted. This difference made the artifact easy to distinguish from random signal noise. The EMA method is more useful than SMA method when the initial value of EMA is located at the first data point and can easily be updated thereafter. The SMA method is less useful because the initial value of SMA is located at the $N^{th}$ point, and the summation of the values of data was required to be completely repeated at each succeeding data point.

Figure 6:
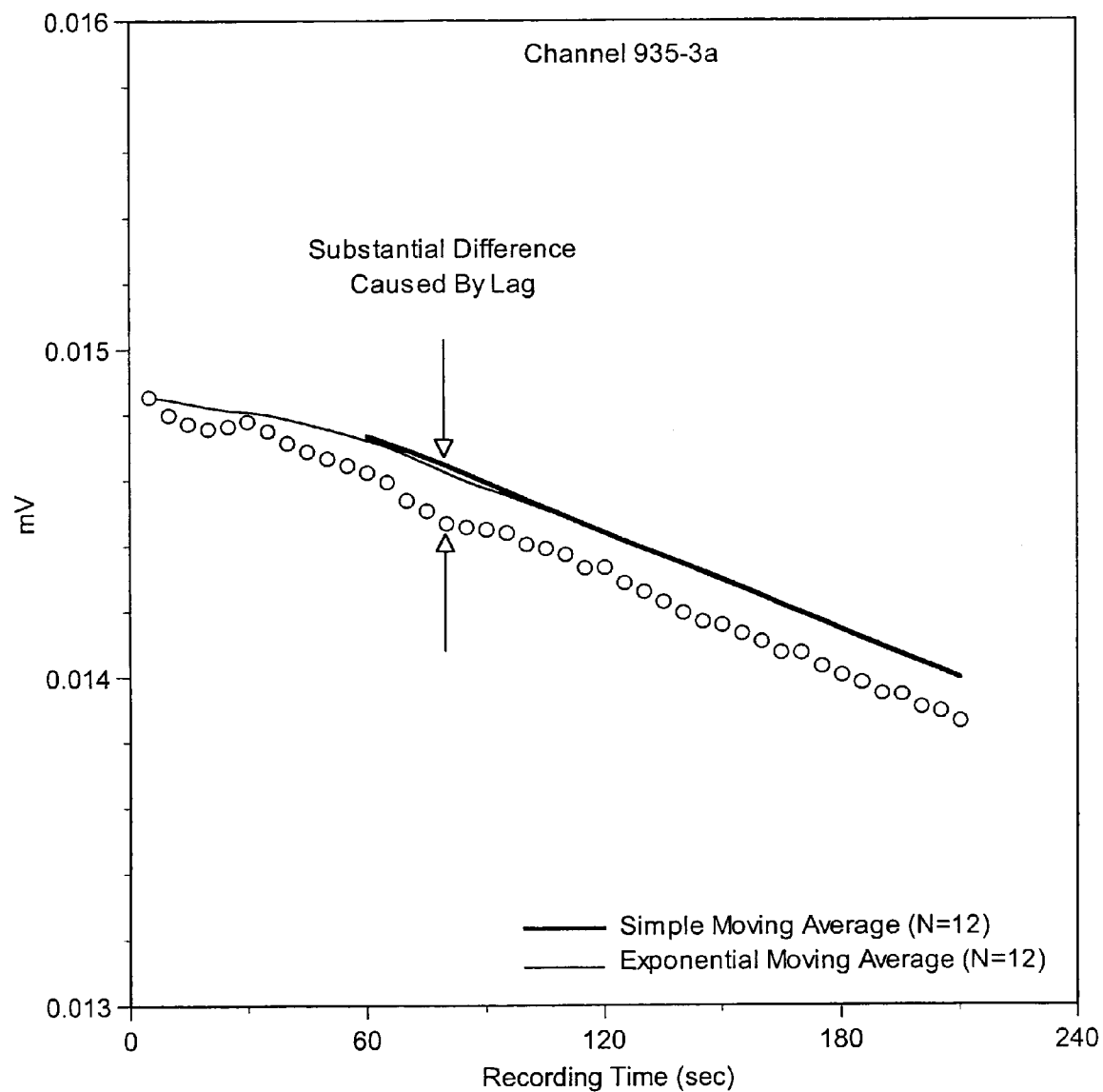
FIG. 6 is a graph illustrating how the conventional moving average lags data that shows a negative trend.

FIG. 6 depicts how the values of EMA and SMA fail to closely follow optical data that do not move in a horizontal trend. The data in FIG. 6 typically exhibit a negative slope when no artifacts are present. The values of EMA and SMA lag far behind the true data despite the smooth and uniform nature of the trend line. This lag is considered unacceptable because it can be mathematically misinterpreted as a data artifact. Furthermore, the magnitude of the lag may vary considerably among different channels and may vary from one measurement to the next, on account of the large variety of optical trends experienced in the apparatus. The variation of the magnitude of the lag suggests that the use of a single, reliable criterion to identify artifacts using the SMA method or the EMA method is not desirable. The method of this invention is better than either the SMA or EMA method.

A common way to compensate for data in trends that are not horizontal is to simply shift the conventional moving average values backwards in time by roughly N/2 points, as required by some data smoothing algorithms. This shift causes the average values to more closely match data that move according to an upward trend or a downward trend. Although this approach has some merit, it has the disadvantage of requiring N/2 data points beyond the current data point to complete the calculations at the current data point. This disadvantage prohibits a real-time calculation of results and is not useful near the end of a data collection session, where future data points are unavailable.

Figure 7:
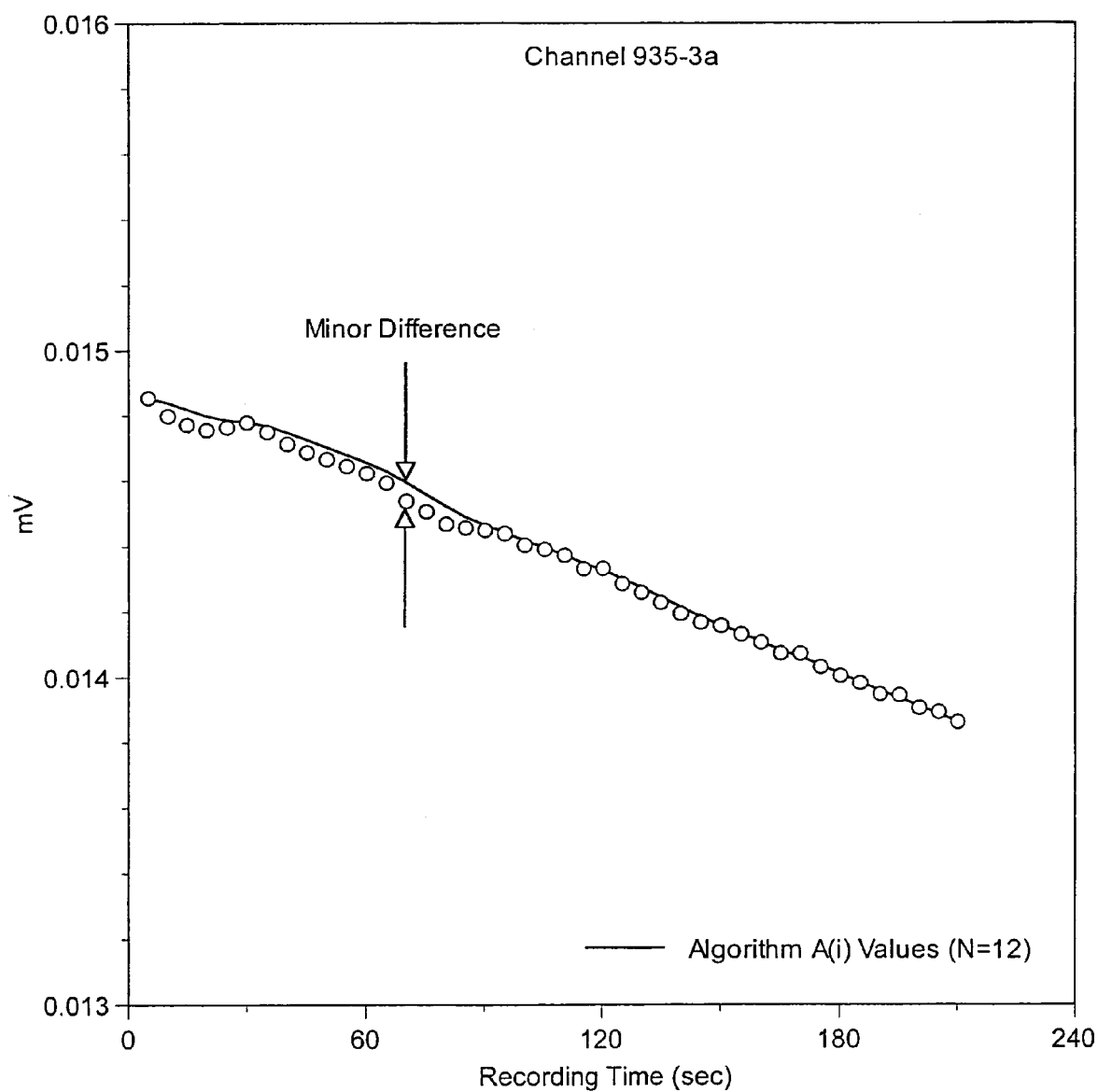
FIG. 7 is a graph illustrating how the moving average of the method of this invention closely follows data that shows a negative trend.

FIG. 7 depicts how the method of this invention closely matches the true data from FIG. 6, unlike the SMA and EMA methods. The method of this invention retains the same advantages as the conventional EMA method, namely, the method of this invention is initialized at the first data point and can be updated easily thereafter, requiring no data points beyond the current data point to complete the calculations.

The method of this invention can identify data artifacts resulting from the use of the apparatus described in the patents and patent applications listed previously, which artifacts might compromise results of measurements. Detection of such artifacts can enhance reliability and accuracy of the sensor(s). The method of this invention functions equally well with optical data that exhibit an upward trend, a downward trend, or a horizontal trend during a measurement in which a series of data points are recorded. A conventional moving average algorithm performs well only on data that move according to a horizontal trend. Methods that are accurate and reliable only for a narrow application typically require a precise knowledge of how the data should move during a test. For example, the manner of data movement in a blood oxygen test is well known.

The method of this invention can be used to calculate the values of A(i) in real time, because the method involves a small number of simple equations that require no data points beyond the current data point. The method of this invention is unlike complex methods (such as regression algorithms) that require excessive central processing unit (CPU) time, or methods requiring data points beyond the current data point to complete the calculations (such as some data smoothing algorithms). Instantaneous detection renders a commercial product more desirable by reducing the amount of time wasted during testing.

The method of this invention can be used with apparatus described previously to detect artifacts in recorded optical data to immediately alert the user that a measurement may be erroneous and that a repeat measurement is necessary. On-board software can be used to apply the method of this invention to each individual channel of data and to display the results in real-time on a computer screen display. This method of detection of artifacts is extremely useful for those instances in which the probe is accidentally moved during collection of data, the probe is improperly applied to the surface of the tissue, or any interfering substances come between the probe and the surface of the tissue. Interfering substances include, but are not limited to, body hair, moles, tattoos, scars, dirt, or any other materials that obstruct the light returning from the surface of the tissue and cause rapid perturbations in the recorded data.

The method of this invention is particularly useful for the situation of continuous monitoring of a patient or tracking a sequence of optical signals that do not have a defined periodicity for the purpose of non-invasive determination of the concentration of analytes, such as, for example, hemoglobin, hematocrit, and glucose.

EXAMPLES

The following non-limiting examples show use of the method of this invention to detect artifacts in data obtained by a type apparatus described in U.S. Pat. No. 6,526,298. A prototypical, dual-sensor version of the apparatus was tested on the volar forearms of diabetic patients. In one clinical trial, 20 patients were tested 20 times each (400 total tests). In a second clinical trial, 20 patients were tested 54 times each (1080 total tests). All patients were instructed to remain motionless during each 210-second application of the sensors; however, complete immobilization could not be guaranteed. Each test produced optical data (in millivolt units) from 16 channels per sensor simultaneously at 5-second intervals. The 16 channels were characterized by four (4) wavelengths of light (590 nm, 660 nm, 890 nm and 935 nm) collected at four light collection sites on the surface of the forearm at four (4) locations. The four light collection sites were separated from the light introduction site of the incident beam. The light introduction site was also located on the surface of the forearm. The temperatures of both sensors were set to 30° C. during the first 30 seconds of contact with the forearm. After 30 seconds, the temperature of one sensor was changed linearly to 20° C. over 180 seconds, while the temperature of the other sensor was changed linearly to 40° C. over 180 seconds. A total of 32 unique optical measurements were made during each test.

The algorithm was applied to each of the 32 measurements of optical data to detect the presence of artifacts. Before the algorithm was applied, the data for each channel were first normalized to the value recorded at the sixth ($6^{th}$) point (i.e., to the value recorded at the 30-second interval). Normalization allowed all the data to be placed on a common scale of magnitude, thereby simplifying the criteria for artifact detection. The sixth ($6^{th}$) point was selected because it coincided with the time allowed for thermal stabilization between the sensor and tissue (i.e., skin). All empirical calculations of the concentration of the analyte were to begin at this point. Data recorded at points 1 to 5 were considered unimportant and were subsequently excluded from artifact detection. Hence, the algorithm initialized its values at the sixth ($6^{th}$) point recorded for each optical channel. Normalized data (X(i)) were used as the input to the algorithm.

Algorithm input constants were selected as follows:
N=12 points (representing a 60-second time scale)
Dc=0.02 (artifact detection threshold for all 32 data channels)

Example 1

Figure 8A:
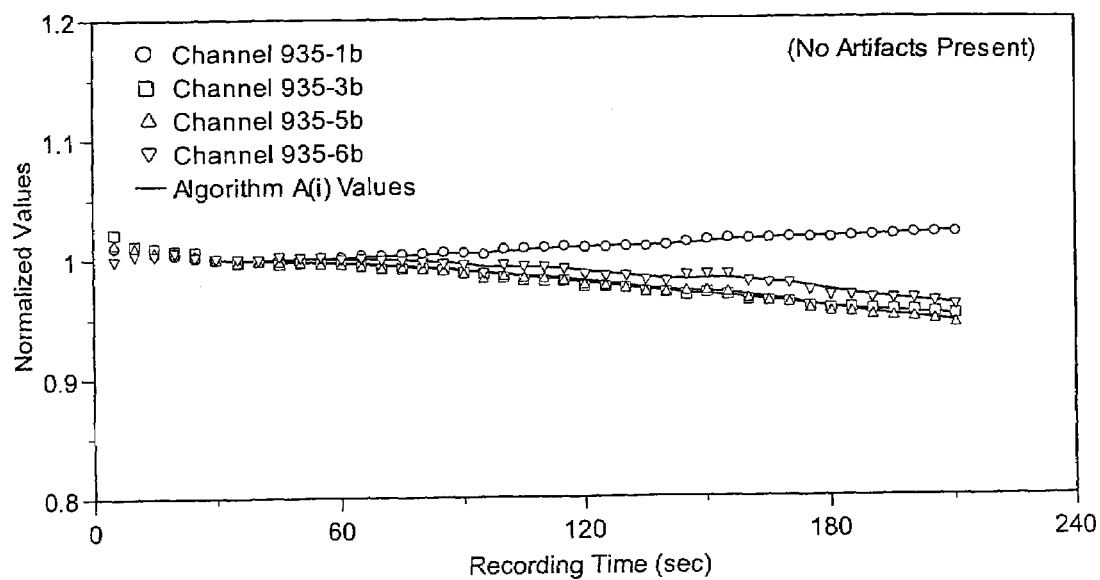
FIGS. 8A and 8B are graphs illustrating how the method of this invention is applied to clinical data. In these figures, no artifacts are present.
Figure 8B:
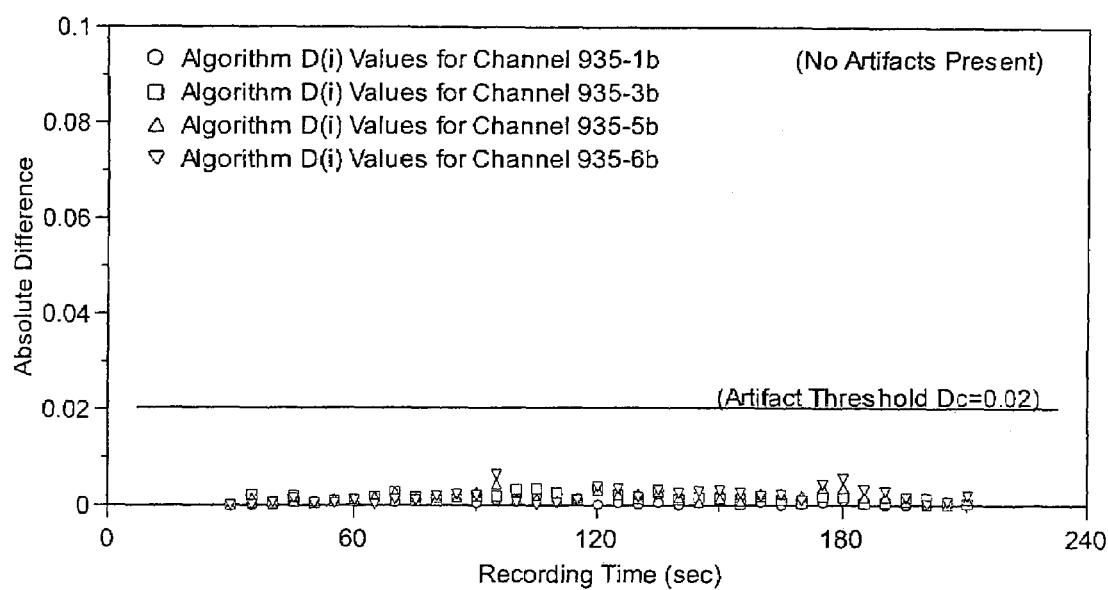

FIG. 8A depicts measurements of normalized optical data recorded on patient no. 11, test no. 17, in the first clinical trial from four (4) of the 32 channels. The values of A(i) closely followed the data beginning with the sixth ($6^{th}$) point. The data were determined to be completely free of artifacts. FIG. 8B depicts the corresponding values of D(i), which represent the absolute difference between each value of A(i) and each value of the normalized data. The values of D(i) remained well below the threshold of 0.02, thereby confirming the absence of artifacts in these measurements.

Example 2

Figure 9A:
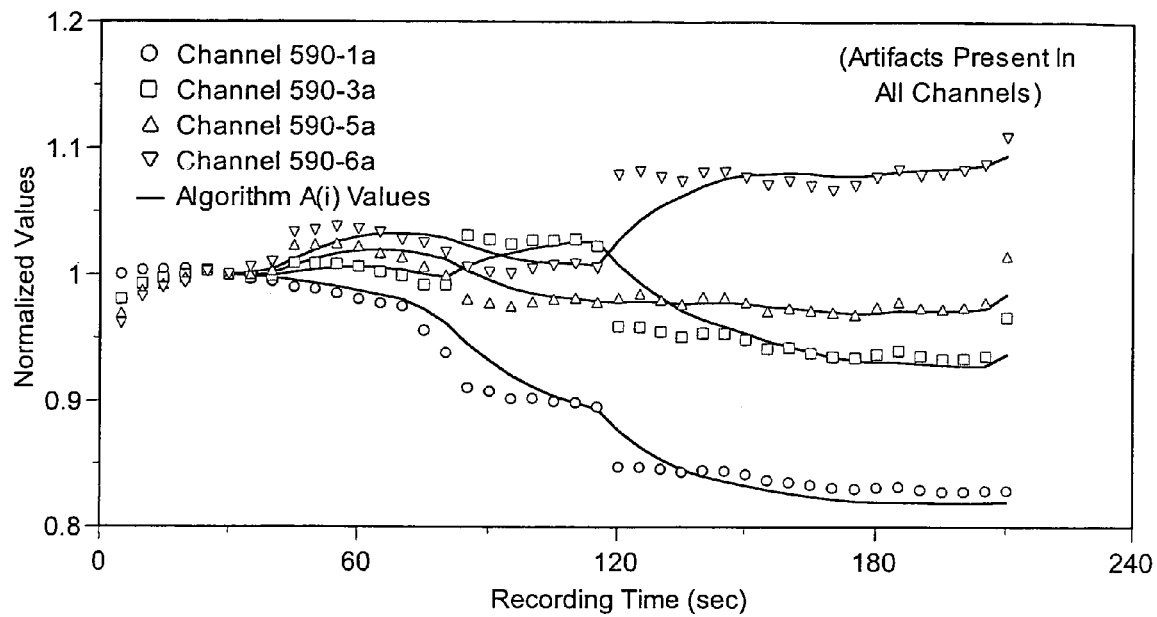
FIGS. 9A and 9B are graphs illustrating how the method of this invention is applied to clinical data. In these figures, artifacts are present.
Figure 9B:
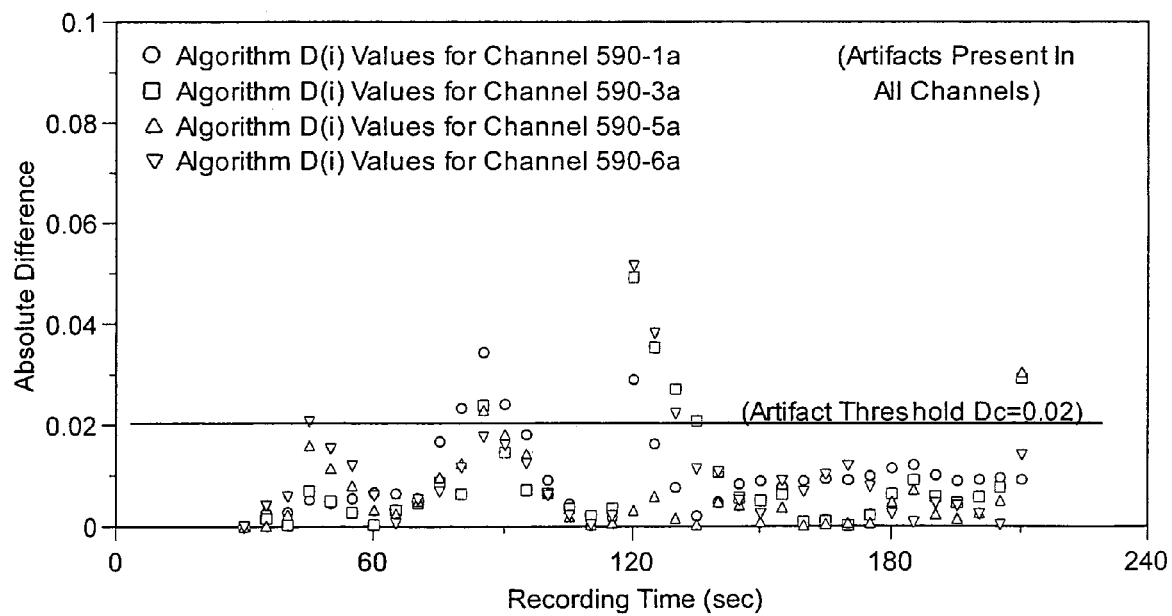

FIG. 9A depicts measurements of normalized optical data recorded on patient no. 10, test no. 9, in the first clinical trial from four (4) of the 32 channels. The values of A(i) failed to closely follow the data at various locations between the sixth ($6^{th}$) point and the end of the test. Data from all four (4) channels were determined to have artifacts at one or more locations. FIG. 9B depicts the corresponding algorithm values of D(i), all of which intermittently exceeded the threshold of 0.02, thereby confirming the presence of artifacts.

Example 3

Figure 10:
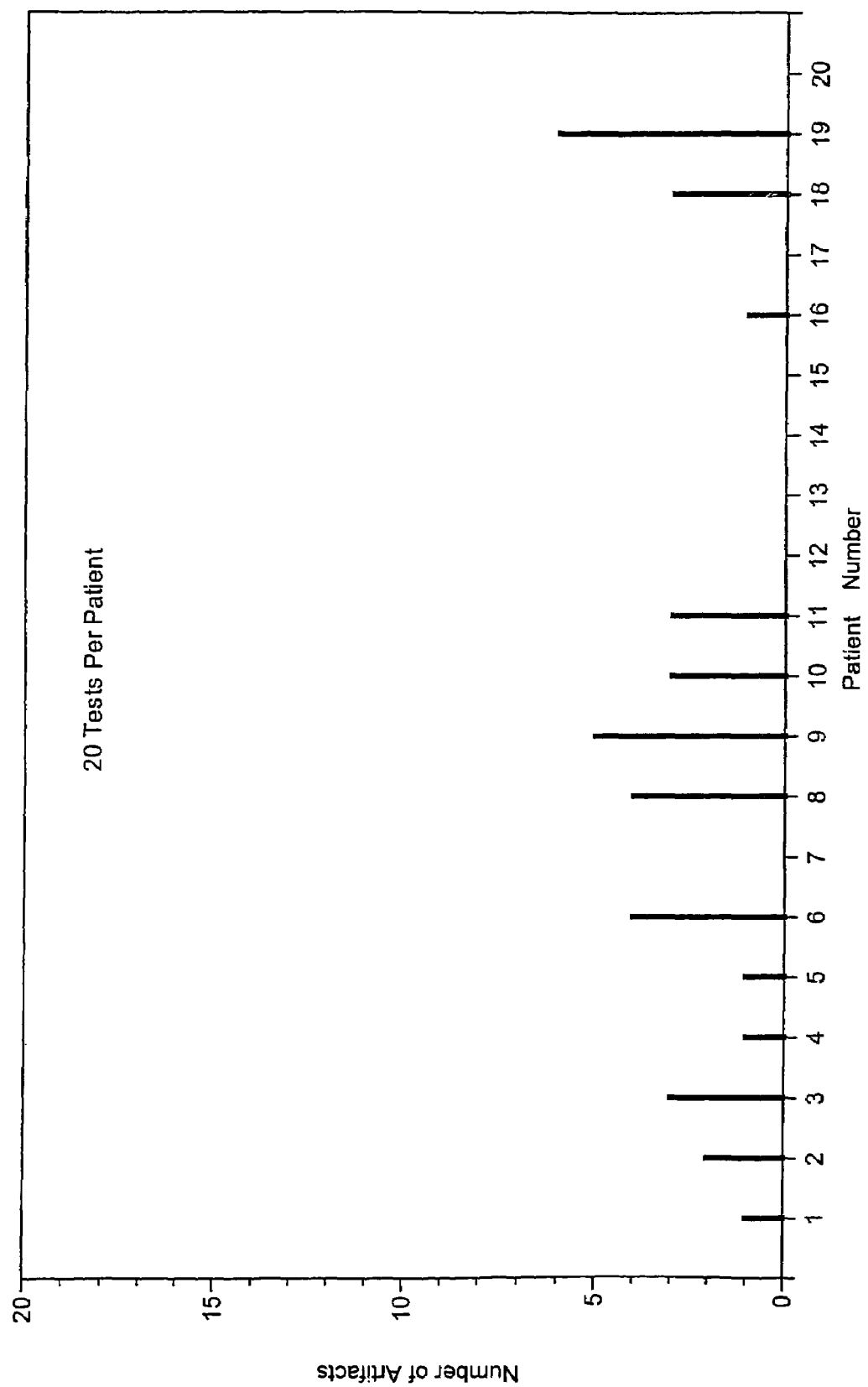
FIG. 10 is a bar graph illustrating the number of tests containing at least one artifact in a first clinical trial.

FIG. 10 summarizes the number of tests in the first clinical trial that contained data artifacts detected by the method of this invention. A total of 37 out of 400 tests were identified as having artifacts in some or all of the measurements taken in the 32 optical channels. Patient no. 19 experienced the highest incidence of artifacts, i.e., 6 artifacts out of 20 tests.

Example 4

Figure 11:
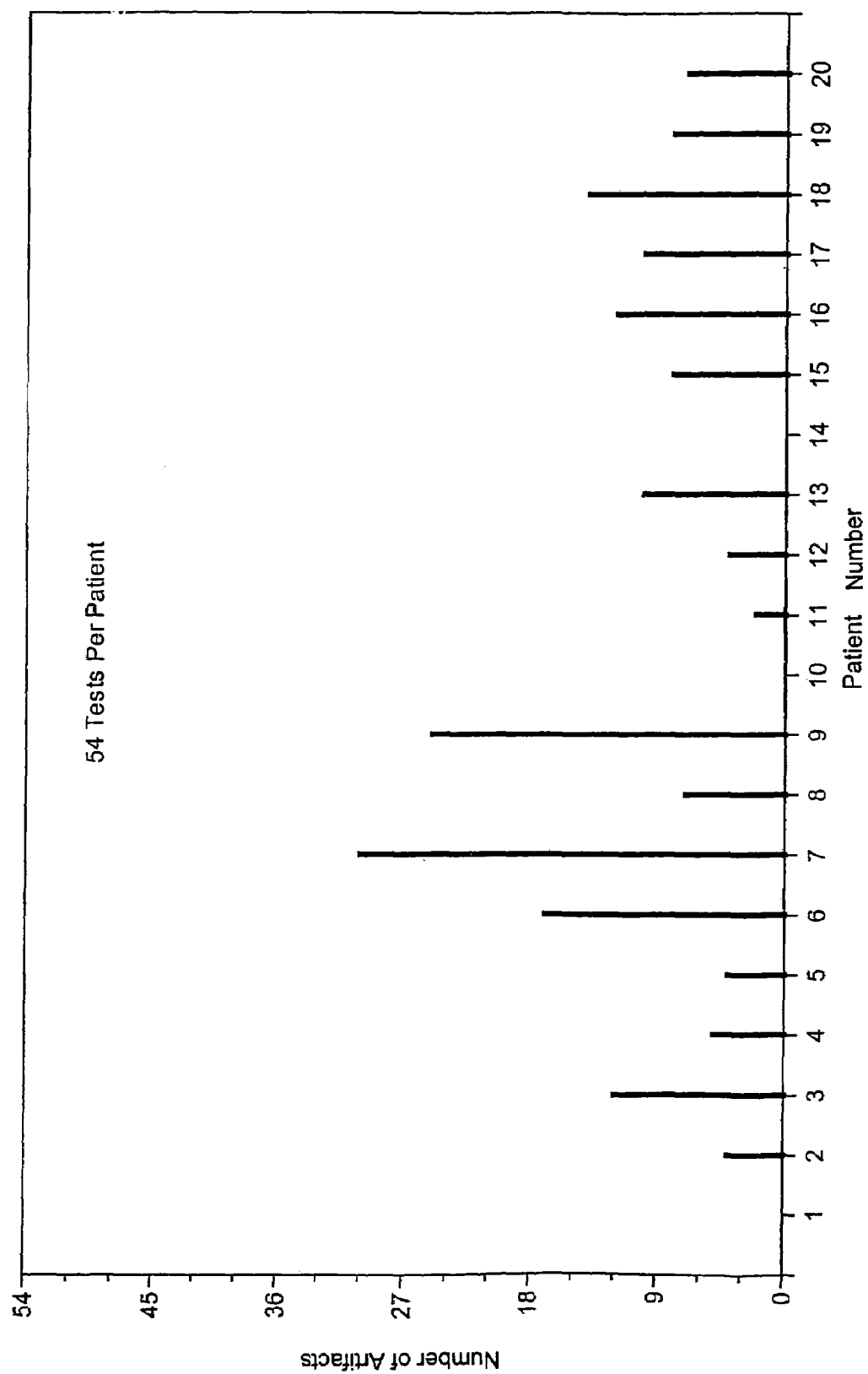
FIG. 11 is a bar graph illustrating the number of tests containing at least one artifact in a second clinical trial.

FIG. 11 summarizes the number of tests in the second clinical trial that contained data artifacts detected by the method of this invention. A total of 179 out of 1080 tests were identified as having artifacts in some or all of the measurements taken in the 32 optical channels. Patient no. 7 experienced the highest incidence of artifacts, i.e., 30 artifacts out of 54 tests.

Example 5

Figure 12:
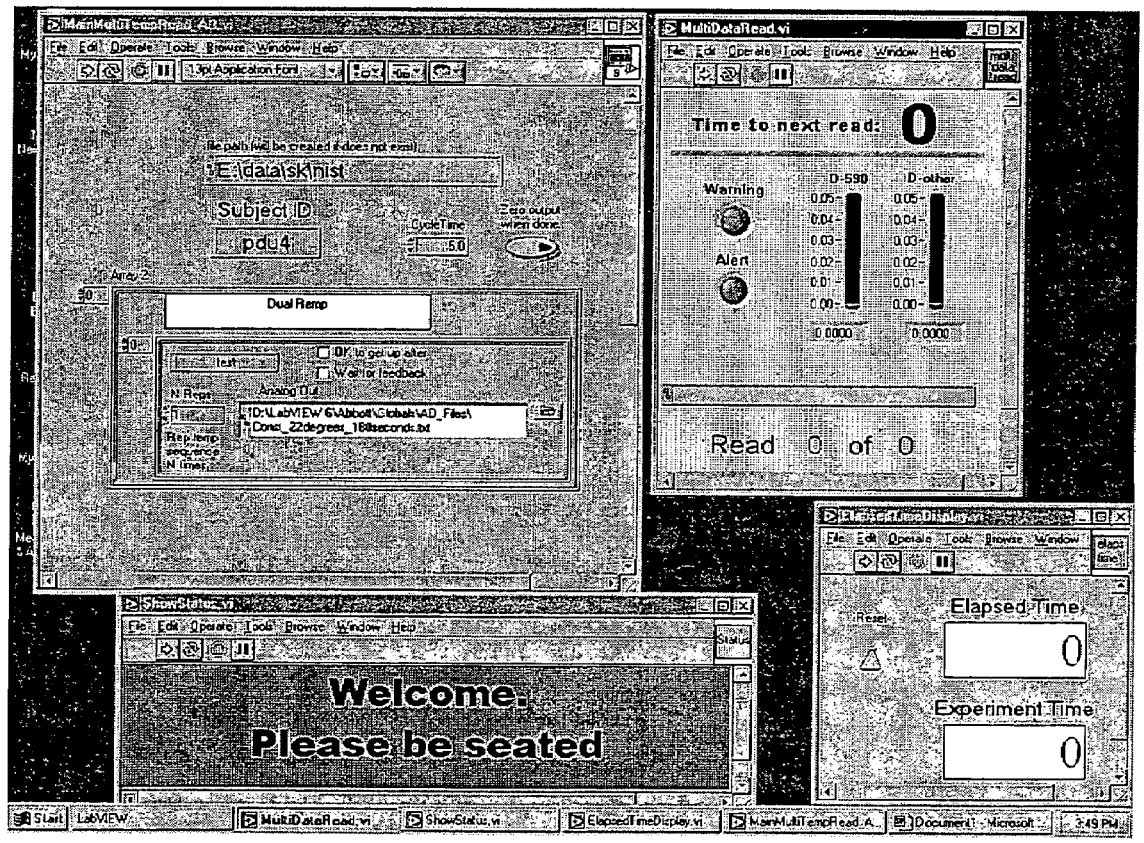
FIG. 12 is a representation of a computer screen display showing the detection of an artifact. In this display, the summary of eight results taken at wavelength of 590 nm and the summary of 24 results taken at other wavelengths are shown.

A demonstration of detection of artifacts in real-time in the apparatus is shown in FIG. 12. The algorithm was coded into the "LabView" processing software during the second clinical trial, and the detection results were displayed in real-time on a computer screen, as illustrated in FIG. 12. The two bar charts displayed a summary of results for the measurements from the 32 optical channels recorded during a test. The bar chart on the left indicated the maximum value of D(i) among the 8 channels at 590 nm wavelength, updated every 5 seconds, as new data were recorded. The bar chart on the right indicated the maximum value of D(i) among the remaining 24 channels, also updated every 5 seconds. The bars also changed color according to the current status of artifact detection: "red" for a detected artifact (D(i)>Dc), "yellow" for an artifact warning level (D(i)>0.015 for the 590 nm wavelength, and D(i)>0.012 for all others), and "green" when the values of D(i) remained below the warning levels. The patient and the clinician could thereby easily see the detection status while the data was being recorded during each 210-second test.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A method for identifying artifacts in optical measurements conducted for the purpose of determination of concentration of an analyte in a tissue, or value of a physiological parameter, or a combination of the forgoing, the method comprising the steps of:
   (a) providing an apparatus for measuring at least one optical property of the tissue;
   (b) introducing electromagnetic radiation at at least one wavelength into the tissue by means of the apparatus;
   (c) collecting optical data from the tissue over a selected period of time;
   (d) introducing the collected data into an algorithm to identify an artifact in the optical data, the artifact resulting from movement of the probe or the tissue during a brief period of time; and
   (e) determining whether an artifact has appeared in the optical data,
   wherein the algorithm utilizes equations for calculating a set of values from the optical data, which optical data comprise a plurality of data points, the equations comprising:

$$S(i) = [1-P] \cdot S(i-1) + P \cdot [X(i) - X(i-1)] \quad (1)$$

$$A(i) = [1-P] \cdot [A(i-1) + S(i)] + P \cdot X(i) \quad (2)$$

$$D(i) = |X(i) - A(i)| \quad (3)$$

Where:
N=effective quantity of data points in the moving average for the algorithm (N=value greater than 1, as specified by user)
Dc=artifact threshold value for D(i) (Dc=value greater than 0, as specified by user)
P=algorithm constant (P=2/[N+1])
i=current data point number (i is greater than 1)
X(i)=value of the current data point
X(i-1)=value of the previous data point
X(1)=value of the first data point
S(i)=value of slope parameter at the current data point
S(i-1)=value of slope parameter at the previous data point
S(1)=value of slope parameter at the first data point (S(1)=0)
A(i) =value of moving average at the current data point
A(i-1)=value of moving average at the previous data point A(1)=value of moving average at the first data point (A(1)=X(1))
D(i)=absolute difference between X(i) and A(i) at the current data point.

2. The method of claim 1, further including the step of (f) providing a signal to an operator to indicate the occurrence of an artifact or to identify optical data that are suspect.

3. The method of claim 1, wherein the optical data comprises reflectance measurements derived from introduction of light at at least one light introduction site by means of at least one light introducing element and collection of light at at least one light collection site by means of at least one light collecting element, the at least one light introducing element and the at least one light collecting element being in contact with the tissue.

4. The method of claim 1, wherein the optical data are collected in a sequential manner to determine a change in blood pressure.

5. The method of claim 1, wherein the optical data are collected in a sequential manner to determine a change in at least one value selected from the group consisting of blood oxygen saturation, the concentration of hemoglobin, value of hematocrit, and the concentration of glucose.

6. The method of claim 1, wherein the electromagnetic radiation has a wavelength in the range of from about 400 nm to about 2200 nm.

7. The method of claim 1, wherein the electromagnetic radiation has a wavelength in the range of from about 400 nm to about 1100 nm.

8. The method of claim 1, wherein the optical data is collected sequentially.

9. The method of claim 1, wherein the algorithm employs a user-selected threshold and the slope parameter to detect motion artifacts in optical signals that do not depend on the periodicity of heartbeats.

10. The method of claim 1, wherein the algorithm is applied to the optical data in real-time.

11. The method of claim 1, further comprising the step of alerting the operator of an occurrence of an artifact.

12. The method of claim 1, further comprising the step of alerting the operator to exclude data that contains an artifact from subsequent calculation.

* * * * *